(12) United States Patent
Washburn

(10) Patent No.: US 10,139,347 B2
(45) Date of Patent: Nov. 27, 2018

(54) MEASUREMENT OF NOBLE GAS ADSORPTION VIA LASER-INDUCED BREAKDOWN SPECTROSCOPY FOR WETTABILITY DETERMINATION

(71) Applicant: Ingrain, Inc., Houston, TX (US)

(72) Inventor: Kathryn Elizabeth Washburn, Houston, TX (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 0 days.

(21) Appl. No.: 15/270,015

(22) Filed: Sep. 20, 2016

(65) Prior Publication Data

US 2017/0082549 A1    Mar. 23, 2017

Related U.S. Application Data

(60) Provisional application No. 62/222,246, filed on Sep. 23, 2015.

(51) Int. Cl.
| | | |
|---|---|---|
| G01N 21/71 | (2006.01) | |
| G01N 21/31 | (2006.01) | |
| G01N 13/00 | (2006.01) | |
| G01N 33/24 | (2006.01) | |

(52) U.S. Cl.
CPC .......... *G01N 21/718* (2013.01); *G01N 13/00* (2013.01); *G01N 33/24* (2013.01)

(58) Field of Classification Search
CPC ....... G01N 21/718; G01N 13/00; G01N 33/24
See application file for complete search history.

(56) References Cited

U.S. PATENT DOCUMENTS

| | | | |
|---|---|---|---|
| 8,081,796 B2 | 12/2011 | Derzhi et al. | |
| 8,170,799 B2 | 5/2012 | Dvorkin et al. | |
| 2004/0195499 A1* | 10/2004 | Ishikawa | G01N 1/2214 |
| | | | 250/281 |
| 2015/0323516 A1 | 11/2015 | Washburn | |
| 2015/0323517 A1 | 11/2015 | Washburn | |

FOREIGN PATENT DOCUMENTS

| | | |
|---|---|---|
| WO | 2004/003595 A1 | 1/2004 |
| WO | 2013/023299 A1 | 2/2013 |
| WO | 2013/071188 A1 | 5/2013 |

OTHER PUBLICATIONS

Fortes et al. "Spectrochemical study for the in situ detection of oil spill residues using laser-induced breakdown spectroscopy" Anal Chim Acta. Dec. 17, 2010;683(1):52-7 Epub Oct. 8, 2010.*

(Continued)

*Primary Examiner* — Dominic J Bologna
(74) *Attorney, Agent, or Firm* — Chamberlain Hrdlicka

(57) ABSTRACT

A method allowing for rapidly determining wettability of porous materials or other materials by measurement of the absorption of noble gases to pore surfaces through laser-induced breakdown spectroscopy is provided. The method can provide an absolute method of quantifying wettability and a method which is a spatially resolved method. A system for performing the method also is provided.

19 Claims, 5 Drawing Sheets

(56) References Cited

OTHER PUBLICATIONS

Prange, "Exploring Hydrophobic Sites in Proteins With Xenon or Krypton", Proteins: Structure, Function, and Genetics 30:61-73 (1998).*

Ito et al. "Determination of colloidal iron in water by laser-induced breakdown spectroscopy" Analytica Chimica Acta vol. 299, Issue 3, Jan. 10, 1995, pp. 401-405. Feb. 14, 2000.*

Anderson, "Wettability Literature Survey—Part 2: Wettability Measurement", Journal of Petroleum Technology, vol. 38, Nov. 1986, pp. 1246-1262.

Koujelev et al., "Artificial Neural Networks for Material Identification, Mineralogy and Analytical Geochemistry Based on Laser-Induced Breakdown Spectroscopy," Artificial Neural Networks—Industrial and Control Engineering Applications, Intech, Apr. 4, 2011, pp. 91-116.

Lalanne et al., "How to Cope with some of the Challenges Associated with Laboratory Measurements on Gas Shale Core Samples," SPE 167709, SPE/EAGE European Unconventional Conference and Exhibition, Vienna, Austria, Feb. 25-27, 2014 (17 pages).

Nordeng, "Evaluating Source Rock Maturity Using Multi-Sample Kinetic Parameters from the Bakken Formation (Miss.-Dev.), Williston Basin, ND," Geol. Investig. No. 164, North Dak. Geol. Survey, 2013, pp. 1-19 (19 pages).

Peters, "Guidelines for Evaluating Petroleum Source Rock Using Programmed Pyrolysis," The American Association of Petroleum Geologist Bulletin, V. 70, No. 3, Mar. 1986, pp. 318-329 (12 pages).

Bellucci et al., "A detailed geochemical investigation of post-nuclear detonation trinitite glass at high spatial resolution: Delineating anthropogenic vs. natural components," Chemical Geology 365, 2014, pp. 69-86 (18 pages).

Tiwari et al., "Detailed Kinetic Analysis of Oil Shale Pyrolysis TGA Data," AIChE Journal, Feb. 2012, vol. 58, No. 2, DOI 10.1002/aic, pp. 505-515 (11 pages).

Lalanne et al., "Benefits of High-Resolution Core Logs Integration in Characterizing Gas Shales Cores", International Symposium of the Society of Core Analysts, SCA Paper No. 2013-076, Sep. 2013 (6 pages).

Grader et al., "Computations of Porosity and Permeability of Sparic Carbonate Using Multi-Scale CT Images," International Symposium of the Society of Core Analysts, SCA2009-Temp Paper #03-10, Sep. 27-30, 2009, pp. 1-10.

* cited by examiner

MEASUREMENT OF NOBLE GAS ADSORPTION VIA LASER-INDUCED BREAKDOWN SPECTROSCOPY FOR WETTABILITY DETERMINATION

This application claims the benefit under 35 U.S.C. § 119(e) of prior U.S. Provisional Patent Application No. 62/222,246, filed Sep. 23, 2015, which is incorporated in its entirety by reference herein.

FIELD OF THE INVENTION

The present invention relates to a rapid method for wettability determination and, in addition, to a method for determining wettability with spatial resolution, and a system for making such determinations, which can be used for determining wettability of porous materials, such as porous geological materials, or other materials.

BACKGROUND OF THE INVENTION

Surface wettability is an important property that influences hydrocarbon flow and production. Wettability is a very important factor in determining the amount of hydrocarbon that may exist in a reservoir, the rate and ease of hydrocarbon production and the ultimate recovery level of hydrocarbons from the reservoir. However, wettability is still poorly understood within porous materials.

Wettability is a surface's preference to be in contact with one fluid over another. Wettability may arise from the surface composition, deposits on the surface and the surface structure. The simplest test for wettability is the contact angle test, where two fluids are placed in contact with the surface and then the contact angle between the surface and a fluid is measured. If the contact angle is low ($\theta<75°$), then the fluid is considered to be wetting. If the contact angle is high ($\theta>105°$), then the fluid is considered non-wetting. If the contact angle is approximately 90° ($75°<\theta<105°$), then the fluid is considered to be neutral wet; neither fluid has a strong preference to be in contact with the surface. If the sample contains two or more distinct wettability types, it is frequently referred to as mixed-wet.

Despite its importance, no good way of measuring wettability within porous materials currently exists. Current methods of measuring wettability for geological samples tend to be unreliable, slow to perform, do not give an absolute wettability value, only relative, and only give a bulk wettability value for the whole sample despite that wettability may vary throughout the pore space.

Wettability testing within porous media is significantly more difficult for numerous reasons. Firstly, direct observation of the fluid contact angle is not possible in many systems due to sample opaqueness and size. Secondly, surface roughness makes it difficult to determine what the true contact angle is. Lastly, the wettability of the sample may not be constant and may vary throughout the sample depending on mineral composition or between pores of similar mineral composition but differing sizes.

The two standard methods within the oil industry for determining the wettability within a porous material are the Amott-Harvey Test and the United States Bureau of Mines (USBM) test. These tests are laboratory methods. The Amott-Harvey test measures wettability by taking a rock core at irreducible water saturation and placing it in water. The amount of water that is spontaneously imbibed is measured. Once spontaneous imbibition has ended, the sample is placed into a centrifuge or flooding apparatus and the amount of water that can be forcibly imbibed into the core is measured. The process is then repeated for oil; the amount of oil that will spontaneously imbibe in the rock is measured and then the amount of oil that can be forcibly imbibed into the core is measured.

The Amott-Harvey test gives the water wetting index by calculating the ratio of the amount of water spontaneously imbibed versus the total amount of water imbibed. Similarly, it gives an oil wetting index by the ratio of the spontaneously imbibed oil to the total amount of oil imbibed. Samples that imbibe neither fluid are considered to be neutral wet. The USBM method for calculation of wettability index does not include the spontaneous imbibition and simply measures the log of the areas between the two forced imbibition steps. Despite their similarities, the two methods may show significant divergence in results for neutral wet and mixed-wet samples.

The Amott-Harvey and USBM methods are frequently combined due to their significant similarities. Neither method gives an absolute value of wettability, but are relative measures that allow petrophysicists to compare the wettability behaviour between different plugs.

Other methods have been developed to try to estimate wettability, however none of these have been considered reliable enough for widespread use. Nuclear magnetic resonance (NMR) is one of the more commonly used alternative techniques. The standard method for wettability determination using NMR is to observe the rate of relaxation of the NMR of different fluids (oil, water, etc.) in a sample compared to their bulk NMR relaxation rates. The relaxation rate of the NMR signal depends on contact of fluid with the surfaces. Fluids near the pore surfaces will also experience higher internal gradients than fluids in the center of pores. Shifts in the relaxation times of different types of fluids or measurement of the amount of internal gradients experienced by the different fluids can be used to estimate which fluid is experiencing the most interaction with the pore surfaces. By seeing which type of fluid experiences the greatest surface contact, the wettability of the system can be estimated. However, these methods are still relative.

Noble gases are hydrophobic and will preferentially adsorb onto hydrophobic surfaces. This tendency has been combined with NMR measurements to observe wettability in samples; signal from the noble gas will decrease when it is adsorbed to a surface such that the loss of noble gas signal can be used to estimate wettability. E.g., T. Prange, M. Schlitz, L. Pernot, R. Fourme, "Exploring hydrophobic sites in proteins with xenon or krypton" Protein Struc. And Bioinform, 30 (1997); G. Pavlovskaya, Z. I. Cleveland, K. F. Stupic, R. J. Basaraba, T. Meersmann, "Hyperpolarized krypton-83 as a contrast agent for magnetic resonance imaging" PNAS, 102 (2005); Z. I. Cleveland, T. Meersmann, "Studying porous materials with krypton-83 NMR spectroscopy", Magn. Reson. Chem, 45, (2007). While the technique works well, the NMR signal from noble gases is quite weak, such that specialized hyperpolarization equipment is needed to improve the signal quality or the measurements must be run at high magnetic field, which requires the use of expensive, superconducting magnets. This makes the technique impractical for a commercial, high throughput environment.

Time-of-flight secondary ion mass spectrometry (TOF-SIMS) has been used to determine contact angle for a variety of different industries such as the semi-conductor and medical industry. The mining industry has used TOF-SIMS to determine surface wettability of geological samples to estimate how well different components will separate during floatation separation. However, this method can only probe the molecular species on the surface of the sample and requires extremely expensive, specialized equipment such that it is not practical on a commercial basis.

Laser induced breakdown spectroscopy (LIBS) uses a laser to ablate a tiny portion of sample. The standard for LIBS uses a q-switched solid state laser that produces a rapid pulse, typically on the order of pico- to nanoseconds in duration. Optics are used to focus the energy onto a single spot on the sample. The laser ablates a small amount of sample at this spot, turning it into a high temperature plasma. The excited atoms then return to a ground state, giving off light of characteristic frequencies. The spot size vaporized by the laser can range in size from a few microns up to hundreds of microns, allowing a large range of resolution and is dependent on the optics of the system. The signal quality improves with larger spot size, but sacrifices resolution. LIBS measurements are frequently performed under an atmospheric purge to avoid unwanted interference from elements in the air. The purge is commonly performed using noble gases, such as helium or argon, as these are not typically elements of interest, though sometimes other gases such as carbon dioxide are used. While a small amount of sample is consumed, the amount is so small that it is considered to be negligible and the technique is considered non-destructive. The wavelength of light from the plasma can be in the 180 to 980 nm region. Detection means may comprise a spectrometer adjusted to a part of the spectral region. The resulting spectra can be analysed by univariate or multivariate data analysis to correlate the spectra to concentration of elements. The spectroscopic analysis of the optical emission in LIBS is different from analytical approaches based on mass spectrometry. Minimal sample preparation is required for LIBS measurements, making it amenable for high-throughput commercial environments.

SUMMARY OF THE INVENTION

A feature of the present invention is a method for rapidly determining wettability of porous materials or other materials by measuring noble gas adsorption at a surface thereof using laser induced breakdown spectroscopy.

A further feature of the present invention is a system for making such determinations in a spatially resolved manner.

Another feature of the present invention is to provide such methods and systems to provide reliable determinations of wettability for porous geological samples, and which give absolute wettability values for the samples.

To achieve these and other advantages and in accordance with the purposes of the present invention, as embodied and broadly described herein, the present invention relates, in part, to a method for determining surface wettability of at least one sample, comprising performing a LIB S measurement under a noble gas atmosphere or purge wherein a surface of the sample is contacted with the noble gas and monitoring the amount of noble gas that has been adsorbed to the sample surface. The LIBS measurement may comprise a single laser shot followed by spectral acquisition of light from the cooling plasma or may comprise a plurality of laser shots, each followed by spectral acquisition. The spectra from each laser shot may be averaged together to improve signal to noise or evaluated individually to determine trends in adsorption behavior with increased laser shot number. A single LIBS measurement may be performed or multiple LIBS measurements may be made, such as measurements performed using two or more noble gases, other types gases (e.g. inert), or other sample states or wettability conditions (e.g. a cleaned sample, restored samples, etc.).

In order to correct for possible effects of pore structure, such as pore volumes, pore surface area, pore shapes, or pore sizes, on the amount of noble gas adsorbed to the sample surface, the LIBS noble gas measurements may be normalized or calibrated to information on pore structure (e.g., pore volumes, pore surface area, pore shapes, or pore sizes), in order to obtain information on the surface wettability. The data on pore volumes, pore surface area, pore shapes, or pore sizes may be measured by but not limited to: X-ray CT, neutron scattering, SEM, FIB-SEM, NMR, BET, nitrogen adsorption, $CO_2$ adsorption, thin section slide microscopy analysis, or mercury injection capillary pressure. The effects of differences in pore volumes, pore surface area, pore shapes, or pore sizes on the amount of adsorbed noble gas may also be compensated for by comparing the LIBS measurements between two or more types of noble gases or one or more noble gas and one or more other type of gas.

As some samples may have two or more distinct wettability states, this effect may be taken into consideration by inputting information on which percentages or portions of the pore space are expected to belong to a particular wetting state (e.g. oil wet). This information may be acquired from a priori information, manually, centrifuge capillary pressure measurements, porous plate measurements, calculated from digital rock physics, mercury injection capillary pressure (MICP), imaging methods (e.g. SEM, X-ray CT, etc.) or NMR measurements. The revised surface area for the differing wettability states can then be used to calculate the expected wettability of a given wetting state.

Furthermore, this present invention can be applied in a spatially resolved manner comprising of a) measuring LIBS spectral data on noble gas adsorption of at least one sample, b) measuring spatial information on the structure at least one sample, c) calculating wettability information on the at least one sample using the noble gas adsorption data, and d) determining spatially resolved wettability information for the at least one sample using the wettability information and the spatial information. Spectral and spatial measurements may be performed on the exact same sample or the spectral measurement can be performed on one sample(s) and the spatial measurement performed on a second sample(s) where samples are of similar composition and structure.

The present invention can relate to a method of analyzing a sample for surface wettability comprising a) introducing a noble gas to a surface of a sample, wherein the gas is capable of contacting the surface, b) measuring LIBS spectral data on a location of the sample contacted with the argon gas, comprising determining at least one emission intensity peak value for at least one preselected wavelength, c) correlating the at least one emission intensity peak value to a measured amount of adsorbed noble gas, and d) relating the measured amount of adsorbed noble gas to at least one wettability property. The LIBS spectral data can be, in various options, spatially resolved, wet surface/non-wet surface allocated, or calibrated or any combination thereof, with reference to at least one of spatial information on pore structure, mixed-wet condition information, wettability information on contact angle or wettability index, respectively, or any combination thereof.

A system for performing the methods is also provided.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

DETAILED DESCRIPTION OF THE INVENTION

Figure 1:
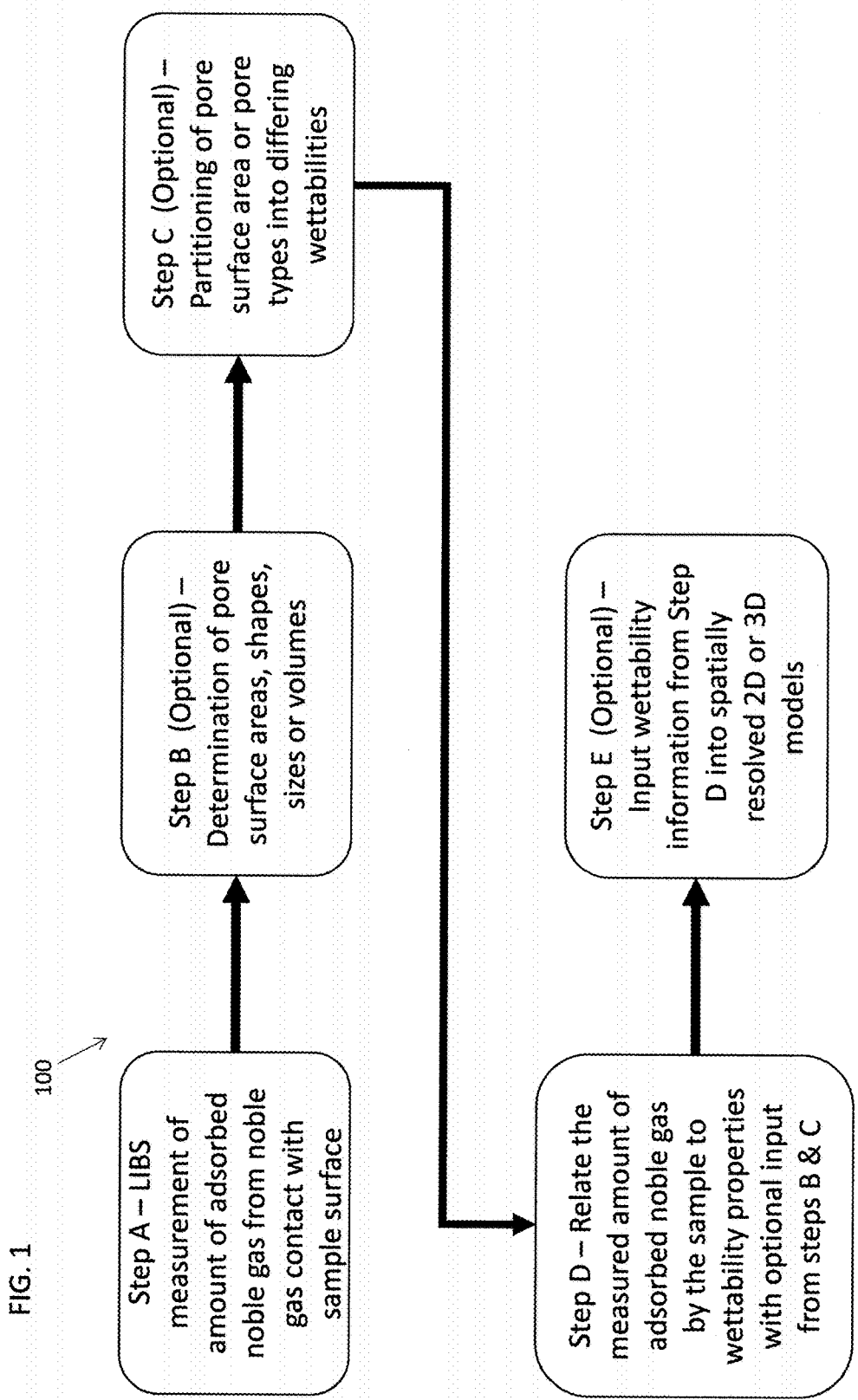
FIG. 1 shows a process flow chart of the determining of sample wettability of a sample according to an example of the present application.

The present invention relates in part to a method which allows for using laser-induced breakdown spectroscopy (LIBS) to observe noble gas adsorption to determine wettability of porous materials or other materials. Noble gases are hydrophobic and flowing or stationary noble gas can selectively adsorb to hydrophobic surface area regions (e.g., organic matter regions) of a surface of a sample at levels, such as in amounts per surface area units, that can be correlated to surface wetting property of the sample. Higher detected emission intensity or intensities by LIBS analysis can be a positive function of higher adsorption levels of a noble gas at the analyzed sample surface. The higher emission intensity, and therefore higher noble gas adsorption level at a LIBS-analyzed sample surface, can correlate to more hydrophobicity of the sample surface, such as compared to a sample displaying lower emission intensity for the noble gas or gases under similar data collection conditions. The method can allow for production of spatially resolved maps of adsorption on the pore surface and provide other advantages and benefits. The method of this invention can help provide absolute values of wettability instead of relative values, and from there, 3D models can be populated with the values measured. This invention can provide an absolute method of quantifying wettability. This invention can also provide an absolute method of quantifying wettability that is a spatially resolved method. The invention also can calibrate the LIBS spectral results with wettability information obtained on the sample with laboratory methods, wherein contact angle or other wettability-indicative properties can be estimated from LIBS spectral measurements. The method of the present invention can provide a rapid alternative to previous wettability determination methods which required a long time to perform, and this invention can be beneficial as a stand-alone service as well as improving fluid flow simulations.

The materials, also referred to herein as the samples, to which the present invention can be applied are not necessarily limited. The materials can be porous materials, such as porous geological materials, e.g., rocks. The kinds of rock to which a method of the present invention can be applied are not necessarily limited. The rock sample can be, for example, organic mud rock, shale, carbonate, sandstone, limestone, dolostone, or other porous rocks, or any combinations thereof, or other kinds. Any source of a rock formation sample of manageable physical size and shape may be used with the present invention. Micro-cores, crushed or broken core pieces, drill cuttings, sidewall cores, outcrop quarrying, whole intact rocks, and the like, may provide suitable rock piece or fragment samples for analysis using methods according to the invention.

The present invention relates in part to a method for determining surface wettability of a sample that includes steps of measuring LIBS spectral data on a sample to calculate the amount of adsorbed noble gas on the pore surface and measuring wettability information on the sample using the LIBS spectral data on the amount of noble gas adsorption.

Furthermore, the present invention relates to measuring LIBS spectral data on the amount of noble gas adsorption in a sample, measuring spatial information on the sample, measuring wettability information on the sample using the LIBS spectral data on the amount of noble gas adsorption, and/or determining spatially resolved wettability information for the sample using the wettability information and/or spatial information. LIBS spectral and spatial measurements may be performed on the exact same sample or the LIBS spectral measurement can be performed on one sample(s) and the spatial measurement performed on a second sample(s) where samples are of similar or of the same composition and structure.

Referring to FIG. 1, a process flow of a method of the present invention is illustrated which can include Steps A, B, C, D and E. The process flow is identified by numeral 100 in the figure. Steps A and D can be required, and Steps B, C and E are optional but can improve the quality of the wettability characterization, such as described herein.

In Step A, spectral data is measured from laser induced breakdown spectroscopy (LIBS) to monitor the amount of noble gas adsorption at the sample surface. This may be performed with a single measurement using a single noble gas, or multiple measurements using two or more noble gases, or multiple measurements using at least one noble gas and other types of gases (e.g. inert), or multiple measurements on different sample conditions (e.g. preserved core versus cleaned core, or restored core versus cleaned core).

Laser induced breakdown spectroscopy (LIBS) uses a laser to ablate a tiny portion of the sample. The standard for LIBS uses a q-switched solid state laser that produces a rapid pulse, typically on the order of pico- to nanoseconds in duration. Optics are used to focus the energy onto a single spot on the sample. The laser ablates a small amount of sample at this spot, turning it into a high temperature plasma. The excited atoms then return to a ground state, giving off light of characteristic frequencies. The spot size vaporized by the laser can range in size from a few microns up to hundreds of microns, allowing a large range of resolution and is dependent on the optics of the system. The signal quality improves with larger spot size, but sacrifices resolution. While a small amount of sample is consumed, the amount is so small that it is considered to be negligible and the technique is considered non-destructive. The wavelength of light from the plasma is in the 200 to 980 nm region. The resulting spectra can be analysed by peak intensity, peak integration, univariate or multivariate data analysis to correlate the spectra to concentration of elements. LIBS has been used previously as a method for mineralogy identification, making it an alternative to X-ray Diffraction (XRD) and X-ray Fluorescence (XRF) methods for mineralogical analysis of samples. It has an advantage over XRF for mineralogical identification because it can measure all elements, whereas XRF is unable to detect light elements. Further, LIBS is able to perform depth profiling, firing the laser in the same spot and observing the different products that are produced with increased depth. LIBS is also very rapid, only taking per seconds per measurement making it amenable for high-throughput industrial use. LIBS measurements can be rastered to produce a two dimensional map of surface composition.

Figure 2:
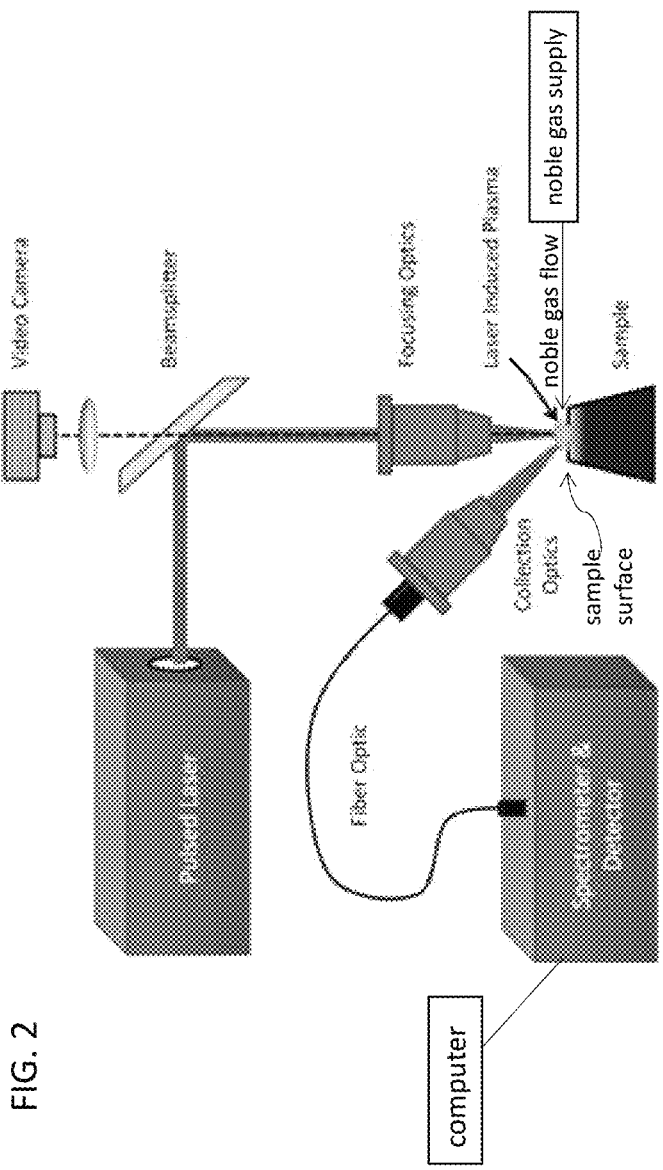
FIG. 2 shows an example setup of laser induced breakdown spectroscopy equipment providing noble gas flow over the sample surface according to an example of the present application.

In accordance with the practice of examples of the present invention, a LIB S analyzer that has the configuration shown in FIG. 2 was used. The LIBS analyzer used was commercially obtained from TSI Incorporated. The measurements were performed on the company's (TSI) latest model of LIBS analyzer and has the name ChemReveal. Measurements were made using a 200 mJ laser operating at 36 mJ power. Shot rate was 5 Hz and laser duration was 8 nanoseconds (ns). Laser spot size on the sample was 400 micrometers ($\mu m$). Samples were placed on a three axis adjustable stage. A high-resolution camera was used to adjust the sample stage to the correct distance for measurement and see where on the sample the laser would be fired. Argon was supplied to continuously flow over the sample before measurement at a flow rate of from about 10 to about 12 liter/minute for a time period of from about 20 to about 30 seconds prior to directing any laser shots onto the surface of the sample. Argon flow over the sample was continued during LIBS measurement to avoid unwanted influence of elements commonly present in air (H, N, O, etc.) in the measurement. About 150 shots of the laser, including acquisition of the light spectra after each laser shot, were measured. This appears to be adequate for most samples, though more or fewer shots can be used. Some samples may show a decrease in argon content with laser shot number, others may show a level behavior, or possibly an increase. Analysis of the data may use all the acquired spectra or may be limited to a subset of the acquired spectra. Under at least these operational conditions, argon sourced from the argon purge gas was found to adsorb to the surface of the sample in amounts that can be emitted by LIBS in quantifiably detectable intensities. For purposes of the present invention, each of the operating parameters, type of gas, and set up can be varied, such as operation at ranges above or below the number ranges provided above.

Though argon gas was used in this example, other noble gases can be used, such as neon, xenon, helium, or krypton, or combinations of any of these and/or different flow rates can be used. Different stable isotopic forms of any of the noble gases can be used provided that they have detectable emission wavelengths by LIBS analysis from flow of the noble gas over the surface of the sample. For argon, for example, $^{40}Ar$ can be used or other isotopes of the element.

Optionally, one or more cleaning shots can be made on the sample during the argon gas flow over the sample before the LIBS measurement. The sample may be subjected to cleaning shots as-is without the need for any additional previous or subsequent sample preparation before the sample is subjected to the measurement shots. Cleaning shots may be performed in order to remove surface imperfections or contaminants, but a weak power setting typically is used for the cleaning shots in order to avoid pyrolysation of the nearby organic matter. In the measurement shots, the LIBS spot focus can be solely on organic matter of the sample, the spot focus can solely be on the inorganic matter of the samples, or the spot can focus on both organic and inorganic matter. The contribution of the organic matter may be deconvoluted through manual or uni or multivariate analysis or cluster analysis or self-organising maps or neural nets or metaheuristic procedures (e.g. particle swarm optimization, genetic algorithms, etc.). As indicated, the argon adsorbs to hydrophobic surface areas of the sample, which commonly includes organic matter. A single LIBS measurement or multiple LIBS spectral measurements can be used for the analysis.

In LIBS, the light emitted from the plasma as it cools is measured. Depending on the noble gas or gases used, the measured light is usually in the wavelength range of 200 to 980 nm. Noble gases, like certain other elements, will have peaks located at distinctive wavelengths. Sometimes there exists multiple peaks for a given element, though frequently one peak of an element is more desirable for analysis (e.g. stronger intensity, fewer nearby peaks that could interfere) than other peaks produced by that element. Intensity peaks for different noble gases, such as argon, can be plotted as intensity (arbitrary units, a.u.) versus wavelength (nm).

Figure 3:
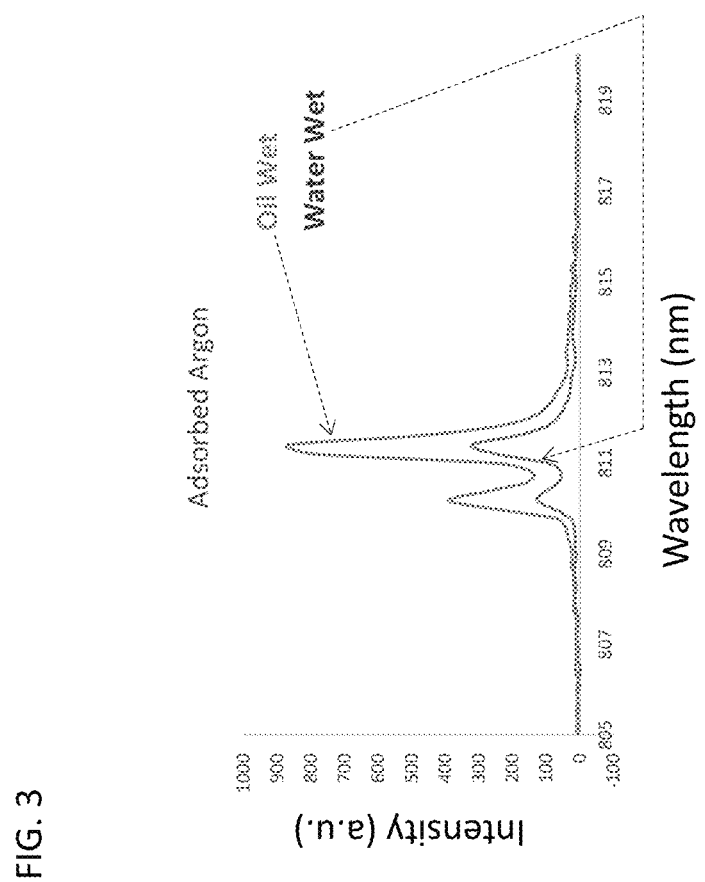
FIG. 3 shows the relative LIBS peak intensities of argon from a hydrophilic and hydrophobic surface according to an example of the present application.

FIG. 3 shows spectra of peaks associated with argon for two surfaces of differing wettability. Argon gas, for example, can have emission intensity peaks centered near wavelengths of 810 nm and 812 nm, as shown in FIG. 3. The hydrophobic (i.e., oil wet) surface shows a higher amount of argon adsorption than the hydrophilic (i.e., water wet) surface.

Figure 4:
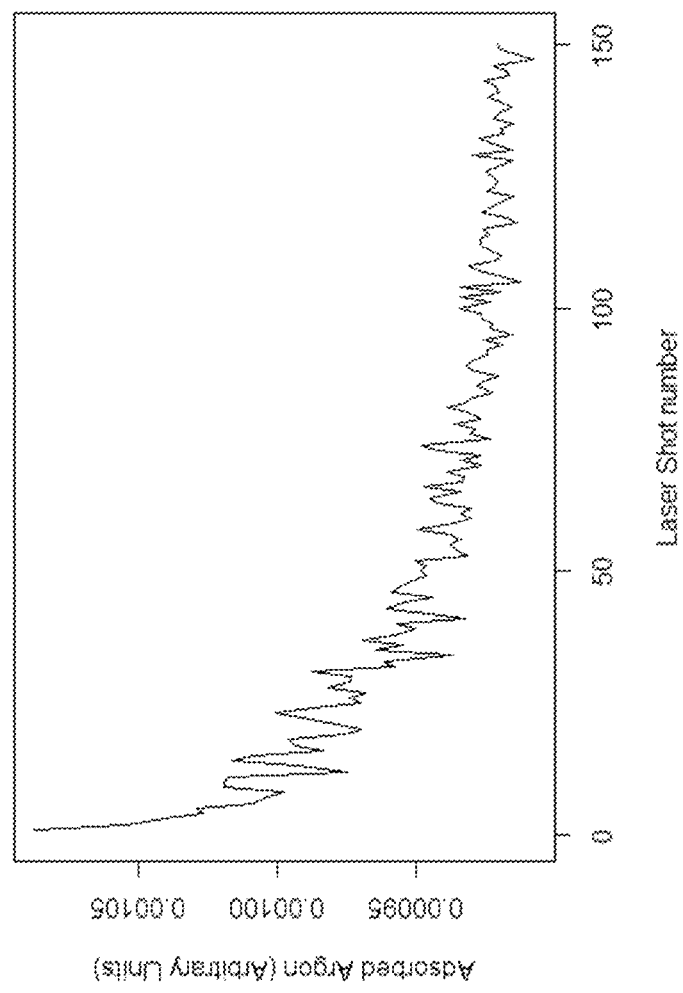
FIG. 4 shows the change in amount of adsorbed argon with laser shot number for an organic rich shale sample according to an example of the present application.

FIG. 4 shows the change in the amount of adsorbed argon with laser shot number. The laser serves to pyrolyze organic matter in the matrix surrounding the laser aim point. The amount of organic matter decreases with increased laser shot number and this loss is also reflected in the amount of adsorbed argon in the sample.

In Step B, any information on pore structure, such as the pore sizes, shapes, volumes or surface area, used to calibrate or correlate the noble gas data or to create spatially resolved wettability maps is measured. Spatial information can be generated by, but not limited to, X-Ray CT scanning, Scanning Electron Microscopy (SEM), Focused Ion Beam-Scanning Electron Microscopy (FIB-SEM), Nuclear Magnetic Resonance (NMR), Neutron Scattering, Thin Sections (thin section slide microscopy), High Resolution photography, or any equipment capable of generating spatial information. More than one spatial information from various equipment can be used for analysis. The effects of differences in pore volumes, pore surface area, pore shapes, and/or pore sizes on the amount of adsorbed noble gas may also be compensated for by comparing the LIBS measurements between two or more types of noble gases or one or more noble gas and one or more other type of gas.

The samples can undergo LIBS spectral measurement and spatial imaging in the same setup, or the samples can undergo spectral measurement and then are transferred to a second setup for spatial imaging, or the samples can undergo spatial imaging and are then transferred to a second equipment for spectral measurement, or the samples can undergo spectral measurement and spatial imaging and one or more intermediate measurements between the two types of measurements. Spectral and spatial measurements may be performed on the exact same sample or the spectral measurement can be performed on one sample(s) and the spatial measurement performed on a second sample(s) where samples are of similar composition and structure.

In Step C, any information needed in order to modify the expected surface area due to mixed-wet conditions is measured. This may be measured by, but not limited to, a priori information, manually, centrifuge capillary pressure measurements, porous plate measurements, calculated from digital rock physics, mercury injection capillary pressure MICP, imaging methods (e.g. SEM, X-ray CT, etc.), image segmentation, or NMR measurements. Surface areas determined in Step B, for example, can be corrected for mixed-wet conditions at the surface to differentiate between and allocate oil-wetting and water-wetting surface regions at the analyzed portion of the sample. As indicated, the noble gas can selectively adsorb to hydrophobic surface regions of the sample. The source of argon of the emissions detected by LIBS can be predominantly, primarily (e.g., 51% to 99%) essentially all (99%), or exclusively from the oil-wetting regions of the sample surface and not the water-wetting regions thereof. This step can associate the results to the oil-wetting regions, and can avoid averaging the results over the entire surface area including oil-wetting and water-wetting regions. As indicated in FIG. 1, the measured amount of adsorbed noble gas in the sample can be related to wettability properties with optional input from Step B, Step C, or both.

In Step D, wettability information is calculated by relating the amount of noble gas adsorption to information on contact angle, wettability index or indices, or any combination thereof. This information can be produced using calibration data sets developed to relate the amount of one or more adsorbed noble gas or one or more noble gas and one or more type of other gas to samples of known wettability properties. The contact angle and wettability index or indices values of a sample can be determined by laboratory methods. An industry method for determining contact angle is described, for example by Anderson, W. G., "Wettability Literature Survey—Part 2: Wettability Measurement, J. Petro. Tech., Vol. 38, November 1986, pp. 1246-1262. Other industry or laboratory methods in use for these determinations also can be applied. Any single or combination of contact angle, or wettability indices or combination of other wettability metrics can be used. Modifications to pore surface area may be inputted from optional Steps B and/or C.

By calibrating LIBS spectral results with laboratory results for contact angle or another wettability property for a sample, a contact angle of another location on that sample or another sample can be estimated from LIBS spectral measurements, wherein the contact angle is estimated from the amount of noble gas adsorption from the spectral measurements, or wherein univariate or multivariate analysis can be used to correlate the spectral data from one or more noble gas peaks to contact angle.

As to wettability indices, univariate or multivariate analysis can be used to correlate the spectral measurements to wettability derived from Amott-Harvey testing, USBM testing, Amott-USBM testing, or NMR measurement, or other wettability description metrics.

In Step E, and as indicated in FIG. 1, the calculated wettability information can be inputted into and applied to two-dimensional (2D) or three-dimensional (3D) models. Appropriate spatial distribution of wettability in the 2D or 3D models can be determined through image segmentation, assigned manually, determined by capillary pressure simulation or measurements, or determined from previously spatially resolved spectral measurements. Appropriate spatial distribution of contact angles in the 2D or 3D models can be determined through image segmentation, assigned manually, by capillary pressure simulation or measurements, or determined from previously spatially resolved spectral measurements.

Figure 5:
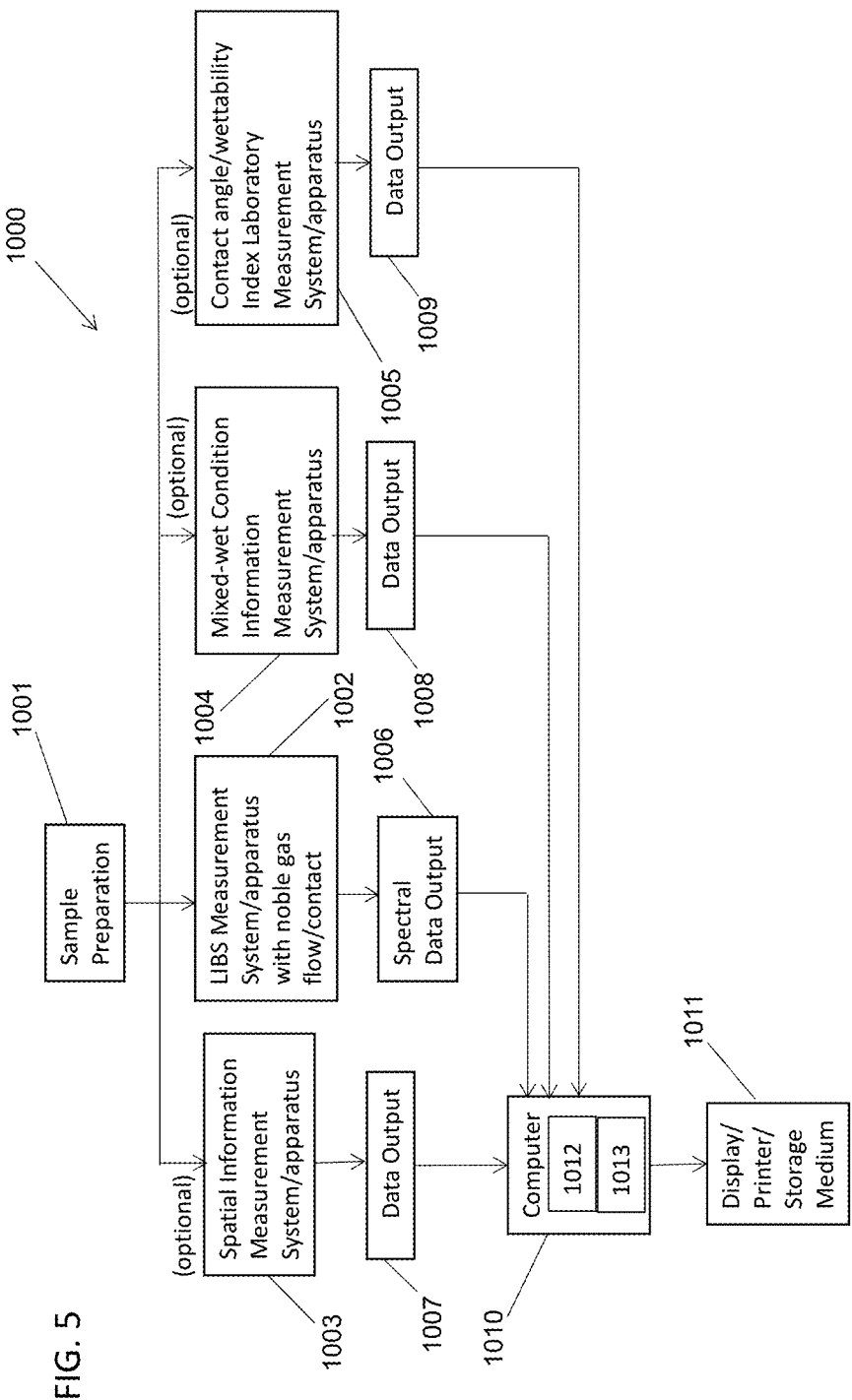
FIG. 5 shows a system according to an example of the present application.

The present invention also relates to a system for determining surface wettability of a sample of petroleum source or reservoir rock, such as according to the processes described herein. As illustrated in FIG. 5, for example, the system 1000 can include a sample preparation station 1001, at least one LIBS Measurement system/apparatus 1002 (e.g., such as shown in more detail in FIG. 2), and optionally also any one, or more or all of a spatial information measurement system/apparatus 1003 (e.g., X-ray CT scanner, SEM, FIB-SEM, NMR, neutron scattering, thin section slide microscopy, high resolution photography), a mixed wet conditions information measurement system/apparatus 1004 (e.g., centrifuge capillary measurement apparatus, porous plate measurement apparatus, MICP, SEM, X-ray CT), and contact angle/wettability index laboratory measurement system/apparatus 1005. The one or more computer systems 1010 can be provided for processing of spectral data 1006 obtained from the LIBS measurement system 1002, and the data output(s) 1007, 1008, and/or 1009 of any of the respective systems 1003, 1004, and 1005 that also may be used, according to methods of the present invention, and to output the results to at least one output device 1011 to display, print, or store results, or any combinations thereof, of the spectral data and results of computations based thereon using a method of the present application. The computer 1010 can comprise at least one memory device 1012 and at least one processor 1013, wherein the memory can include a stored program comprising a set of instructions performed by the processor for executing process steps of the present invention that involve spectral data analysis (e.g., LIBS data analysis) and computations based thereon, and optionally other data analysis and computations based thereon for part or all of the other indicated measurements that can be performed. The computer programs used for spectral data analysis, and optionally other data analysis, and the computations can be stored, as a program product, on at least one non-transitory computer usable storage medium (e.g. a hard disk, a flash memory device, a compact disc, a magnetic tape/disk, or other media) associated with at least one processor (e.g., a CPU) which is adapted to run the programs, or may be stored on an external non-transitory computer usable storage medium which is accessible to the computer processor. Input data and output data, and other program results, or combinations of these also can be stored on the at least one non-transitory computer usable storage medium or other non-transitory storage media. The computer 1010 may include one or more system computers, which may be implemented as a single personal computer or as a network of computers. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The indicated units/equipment of system 1000 can be connected to each other for communications (e.g., data transfer, etc.), via any of hardwire, radio frequency communications, telecommunications, internet connection, or other communication means. The indicated system or apparatus of the present invention may be suitable for analysing material in a laboratory or other space in a building, or in-the-field, such as in a mobile transport vehicle or mechanism on the ground or underground.

The present invention includes the following aspects/embodiments/features in any order and/or in any combination:

1. The present invention relates to a method for determining surface wettability of a sample, comprising:
   a) contacting a surface of at least one sample with noble gas;
   b) measuring LIBS spectral data on the amount or change in amount of surface adsorbed noble gas of the at least one sample;
   c) optionally measuring information on the pore surface area(s), pore size(s), pore shape(s), or pore volume(s) or correction(s) for the pore surface area(s), pore size(s), pore shape(s), or pore volume(s) of at least one sample (e.g., 1 sample, 2 samples, 3 or more samples);
   d) optionally measuring or calculating information on the amount of pore surface area that may belong to different wettability types in a sample due to mixed wettability;
   e) optionally determining wettability information on the at least one sample using calibration data sets developed for LIBS spectral data, with optional input from information on pore surface area(s), pore size(s), pore shape(s), or pore volume(s) and mixed wettability;
   f) optionally determining spatially resolved wettability information for the at least one sample using the wettability information and the spatial information, wherein the sample in b) and the sample in c) are the same or are different but have the same or similar composition and structure.

2. The method of any preceding or following embodiment/feature/aspect, wherein information of the LIBS spectral noble gas adsorption is measured through one or more laser shots each followed by observation of the wavelengths of light emitted by the plasma created by the laser shot.

3. The method of any preceding or following embodiment/feature/aspect, wherein the spatial information on the sample pore surface area, pore sizes, pore shapes, or pore volumes is measured by X-Ray CT scanning, Scanning Electron Microscopy (SEM), Focused Ion Beam-Scanning Electron Microscopy (FIB-SEM), Nuclear Magnetic Resonance (NMR), Neutron Scattering, Thin Section slide microscopy, High Resolution photography, MICP, BET, CO2 adsorption or Nitrogen adsorption or any combinations thereof.

4. The method of any preceding or following embodiment/feature/aspect, wherein the sample undergoes spectral measurement and spatial imaging in the same setup, or the sample undergoes spectral measurement and then is transferred to a second setup for spatial imaging, or the sample undergoes spatial imaging and is then transferred to a second equipment for spectral measurement, or the sample undergoes spectral measurement and spatial imaging and one or more intermediate measurements between the two types of measurements. Spectral and spatial measurements may be performed on the exact same samples or two or more samples of similar or same composition and structure.

5. The method of any preceding or following embodiment/feature/aspect, wherein the wettability information is measured for values of contact angle, wettability index or indices, other wettability metrics, or any combinations thereof.

6. The method of any preceding or following embodiment/feature/aspect, comprising estimating the contact angle from spectral measurements on the sample, wherein the contact angle is estimated from the amount or change in amount of surface adsorbed noble gas in spectral measurements or wherein univariate or multivariate analysis is used to correlate the spectral measurements to contact angle.

7. The method of any preceding or following embodiment/feature/aspect, comprising determining the amount or change in amount of surface adsorbed noble gas in spectral measurements to correlate the spectral measurements to wettability derived from Amott-Harvey testing, USBM testing, Amott-USBM testing, NMR measurement, or other wettability description metrics.

8. The method of any preceding or following embodiment/feature/aspect, comprising determining wettability wherein univariate or multivariate analysis is used to correlate the amount or change in amount of surface adsorbed noble gas in spectral measurements to wettability derived from Amott-Harvey testing, USBM testing, Amott-USBM testing, NMR measurement, or other wettability description metrics.

9. The method of any preceding or following embodiment/feature/aspect, wherein the wettability information measured from the LIBS measurement of the amount or change in amount of adsorbed noble gas is inputted into at least one of spatial distribution of wettability indices in 2D or 3D models, or spatial distribution of contact angles in 2D or 3D models, or spatial distribution of other wettability description metrics into 2D or 3D models.

10. The method of any preceding or following embodiment/feature/aspect, wherein the spatial distribution of wettability indices in the 2D or 3D models is determined through image segmentation, assigned manually, determined by capillary pressure simulation or measurements, or determined from previously spatially resolved spectral measurements.

11. The method of any preceding or following embodiment/feature/aspect, wherein the spatial distribution of contact angles in the 2D or 3D models is determined through image segmentation, assigned manually, by capillary pressure simulation or measurements, or determined from previously spatially resolved spectral measurements.

12. The method of any preceding or following embodiment/feature/aspect, wherein the spatial distribution of other wettability description metrics in the 2D or 3D models is determined through image segmentation, assigned manually, by capillary pressure simulation or measurements, or determined from previously spatially resolved spectral measurements.

13. The method of any preceding or following embodiment/feature/aspect, wherein the sample is a porous sample.

14. The method of any preceding or following embodiment/feature/aspect, wherein the sample is a porous geological sample.

15. The method of any preceding or following embodiment/feature/aspect, wherein the sample is shale.

16. The method of any preceding or following embodiment/feature/aspect, wherein the noble gas is introduced to the surface in continuous flow before and during the LIBS spectral data measurements.

17. The method of any preceding or following embodiment/feature/aspect, wherein the noble gas is argon, neon, xenon, helium, krypton, singly or in combinations of different isotopes of the same elemental kind of noble gas or in combinations of different elemental kinds of noble gases.

18. The method of any preceding or following embodiment/feature/aspect, wherein the noble gas comprises a single elemental kind and single isotope of a noble gas (e.g., $^{40}$Ar or others).

19. A method of analyzing a sample for surface wettability comprising:
   a) introducing at least one noble gas to a surface of a sample, wherein the gas is capable of contacting the surface;

b) measuring LIBS spectral data on a location of the sample contacted with the noble gas, comprising determining at least one emission intensity peak value for at least one preselected wavelength;

c) correlating the at least one emission intensity peak value to a measured amount of adsorbed noble gas; and d) relating the measured amount of adsorbed noble gas to at least one wettability property.

20. The method of any preceding or following embodiment/feature/aspect, further comprising e) spatially resolving, wet surface/non-wet surface allocating, or calibrating or any combination thereof, the LIBS spectral data with reference to at least one of spatial information on pore structure, mixed-wet condition information, wettability information on contact angle or wettability index, or any combination thereof.

21. A system to perform the method of any preceding claim.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for determining surface wettability of a sample, comprising:
   a) contacting a surface of the sample with noble gas;
   b) measuring LIBS spectral data on an amount of noble gas or a change in the amount of noble gas that is adsorbed by the sample;
   c) measuring spatial information on pore surface area, pore size, pore shape, pore volume, correction for the pore surface area, the pore size, the pore shape, or pore volume of the sample, or a second sample that has a similar composition and structure;
   d) measuring or calculating information on an amount of pore surface area for each different wettability type the sample, wherein the sample comprises mixed wettability;
   e) determining wettability information on the at least one sample using calibration data sets developed for LIBS spectral data, with input from information on pore surface areas, pore sizes, pore shapes, or pore volumes and mixed wettability;
   f) determining spatially resolved wettability information for the sample or the second sample using the wettability information and the spatial information.

2. The method of claim 1, wherein measuring the LIBS spectral data comprises creating plasma with one or more laser shots directed at the sample or the second sample, each laser shot followed by observation of the wavelengths of light emitted by the plasma.

3. The method of claim 1, wherein measuring the spatial information comprises X-Ray CT scanning, Scanning Electron Microscopy (SEM), Focused Ion Beam-Scanning Electron Microscopy (FIB-SEM), Nuclear Magnetic Resonance (NMR), Neutron Scattering, Thin Section slide microscopy, High Resolution photography, mercury injection capillary pressure (MICP), CO2 adsorption, Nitrogen adsorption, or any combinations thereof.

4. The method of claim 1, wherein the sample undergoes spectral measurement and spatial imaging in a single setup, or measuring the LIBS spectral data of the sample in a first setup and transferring the sample to a second setup for spatial imaging, or measuring spatial information on the sample at a first equipment and transferring the sample to a second equipment for spectral measurement, or measuring the LIBS spectral data and the spatial information on the sample and measuring one or more intermediate measurements between the measuring of the LIBS spectral data and the spatial information, wherein the measuring is performed on the sample, the second sample, or additional samples of similar or same composition and structure.

5. The method of claim 1, wherein the determining the wettability information comprises measuring for values of contact angle, wettability index or indices, other wettability metrics, or any combinations thereof.

6. The method of claim 1, comprising estimating the contact angle from spectral measurements on the sample, wherein the contact angle is estimated from the amount or change in amount of noble gas in spectral measurements, or wherein univariate or multivariate analysis is used to correlate the spectral measurements to contact angle.

7. The method of claim 1, comprising determining an amount or change in amount of surface-adsorbed noble gas in spectral measurements to correlate the spectral measurements to wettability derived from Amott-Harvey testing, USBM testing, Amott-USBM testing, NMR measurement, or other wettability description metrics.

8. The method of claim 1, comprising determining wettability wherein univariate or multivariate analysis is used to correlate the amount or change in amount of noble gas in spectral measurements to wettability derived from Amott-Harvey testing, USBM testing, Amott-USBM testing, NMR measurement, or other wettability description metrics.

9. The method of claim 1, comprising inputting the wettability information spatial distribution of wettability indices in 2D or 3D models, spatial distribution of contact angles in 2D or 3D models, spatial distribution of other wettability description metrics into 2D or 3D models, or any combination thereof.

10. The method of claim 9, wherein the spatial distribution of wettability indices in the 2D or 3D models is determined through image segmentation, assigned manually, determined by capillary pressure simulation or measurements, or determined from previously spatially resolved spectral measurements.

11. The method of claim 9, wherein the spatial distribution of contact angles in the 2D or 3D models is determined through image segmentation, assigned manually, by capillary pressure simulation or measurements, or determined from previously spatially resolved spectral measurements.

12. The method of claim 9, wherein the spatial distribution of other wettability description metrics in the 2D or 3D models is determined through image segmentation, assigned manually, by capillary pressure simulation or measurements, or determined from previously spatially resolved spectral measurements.

13. The method of claim 1, wherein the sample is a porous sample.

14. The method of claim 1, wherein the sample is a porous geological sample.

15. The method of claim 1, wherein the sample is shale.

16. The method of claim 1, comprising introducing the noble gas to the surface in continuous flow before and during the LIBS spectral data measurements.

17. The method of claim 1, wherein the noble gas is argon, neon, xenon, helium, krypton, singly or in combinations of different isotopes of the same elemental kind of noble gas or in combinations of different elemental kinds of noble gases.

18. The method of claim 1, wherein the noble gas comprises a single elemental kind and single isotope of a noble gas.

19. A method of analyzing a sample for surface wettability comprising:

a) introducing at least one noble gas to a surface of a sample, wherein the gas is capable of contacting the surface;

b) measuring LIBS spectral data on a location of the sample contacted with the noble gas, comprising determining at least one emission intensity peak value for at least one preselected wavelength;

c) correlating the at least one emission intensity peak value to a measured amount of adsorbed noble gas;

d) relating the measured amount of adsorbed noble gas to at least one wettability property;

e) spatially resolving, wet surface/non-wet surface allocating, or calibrating or any combination thereof, the LIBS spectral data with reference to at least one of spatial information on pore structure, mixed-wet condition information, wettability information on contact angle or wettability index, or any combination thereof.

* * * * *